(12) United States Patent
Hatayama et al.

(10) Patent No.: US 9,022,941 B2
(45) Date of Patent: May 5, 2015

(54) ULTRASONIC DIAGNOSTIC APPARATUS AND CARRIER SIGNAL GENERATING CIRCUIT

(75) Inventors: Kanako Hatayama, Tokyo (JP); Kenji Maio, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 390 days.

(21) Appl. No.: 13/259,347

(22) PCT Filed: Apr. 1, 2010

(86) PCT No.: PCT/JP2010/055997
§ 371 (c)(1),
(2), (4) Date: Sep. 23, 2011

(87) PCT Pub. No.: WO2010/114086
PCT Pub. Date: Oct. 7, 2010

(65) Prior Publication Data
US 2012/0029351 A1 Feb. 2, 2012

(30) Foreign Application Priority Data

Apr. 2, 2009 (JP) ................................. 2009-090099

(51) Int. Cl.
| | | |
|---|---|---|
| *A61B 8/14* | (2006.01) | |
| *B06B 1/02* | (2006.01) | |
| *G01S 7/52* | (2006.01) | |
| *A61B 8/00* | (2006.01) | |

(52) U.S. Cl.
CPC ............. *B06B 1/0207* (2013.01); *G01S 7/5202* (2013.01); *A61B 8/00* (2013.01); *B06B 2201/76* (2013.01); *Y10S 367/903* (2013.01)

(58) Field of Classification Search
None
See application file for complete search history.

(56) References Cited

U.S. PATENT DOCUMENTS 4,805,458 A * 2/1989 Yoshie ............................ 73/602
4,926,380 A * 5/1990 Harada ............................ 367/7

FOREIGN PATENT DOCUMENTS

| JP | 62-117533 | 5/1987 |
|---|---|---|
| JP | 9-234202 | 9/1997 |
| JP | 10-5218 | 1/1998 |
| JP | 11-56839 | 3/1999 |

* cited by examiner

*Primary Examiner* — Unsu Jung
*Assistant Examiner* — Saurel J Selkin
(74) *Attorney, Agent, or Firm* — Brundidge & Stanger, P.C.

(57) ABSTRACT

In order to simplify a manufacturing process and reduce cost and power consumption by providing an ultrasonic diagnostic apparatus including a carrier signal generating circuit excellent in IC implementation, a carrier signal generating circuit for generating an output voltage Vo applied to an ultrasonic probe 41 includes cascaded source follower type NMOSFETs 11 to 14, a variable current source 31, and a constant current source for biasing 32. The probe 41 can be made to generate the output voltage Vo with arbitrary amplitude by controlling a gate voltage V4 by controlling the output current value of the variable current source 31. In addition, a voltage applied to each NMOSFET can be divided by connecting the NMOSFETs 11 to 14 in a multi-stage manner. Accordingly, the withstand voltage of the NMOSFET may be low.

6 Claims, 9 Drawing Sheets

ULTRASONIC DIAGNOSTIC APPARATUS AND CARRIER SIGNAL GENERATING CIRCUIT

TECHNICAL FIELD

The present invention relates to an ultrasonic diagnostic apparatus which forms a tomographic image or the like of a body with a received signal obtained by transmitting an ultrasonic wave to the body and in particular, a signal transmission technique of generating an arbitrary transmission signal waveform applied to an ultrasonic probe.

BACKGROUND ART

Conventionally, a sine wave or a rectangular wave with about 100 Vpp and about several megahertz to 20 MHZ is used for driving an ultrasonic probe of an ultrasonic diagnostic apparatus. For this reason, as a simple method of generating such a high-voltage carrier pulse from a transmitter circuit, which transmits an ultrasonic wave, of an ultrasonic wave transceiver unit, a method of providing an electronic switch in each of positive and negative DC high voltage supplies Vp and Vn and performing alternate switching thereof is known (refer to PTL 1). Generally, a P type MOS transistor (hereinafter, a PMOS) and an N type MOS transistor (hereinafter, an NMOS) have been used for fast switching using such electronic switches.

CITATION LIST

Patent Literature

[PTL 1] JP-A-9-234202

SUMMARY OF INVENTION

Technical Problem

However, the above conventional technique has the following problems.

(1) Since there are only two values of Vp and Vn as an output pulse voltage, it is not possible to support an ultrasonic diagnostic apparatus for which an arbitrary level is requested.

(2) Since both a PMOS and an NMOS are needed, the manufacturing process becomes complicated when fabricating an IC. This is not economical.

(3) Although a high withstand voltage is required for both the PMOS and the NMOS, the semiconductor chip size is large in the case of a MOS with a high withstand voltage. Accordingly, it is not appropriate to mount many switches in one chip.

In order to solve the problem described above, it is an object of the invention to provide an ultrasonic diagnostic apparatus including a transmitter circuit for generation of a carrier signal, which is excellent in IC implementation, and a carrier signal generating circuit.

Solution to Problem

In order to achieve the above-described object, in the invention, there is provided an ultrasonic diagnostic apparatus including: a probe which transmits and receives an ultrasonic wave to and from an object; a transmitter circuit unit that supplies a voltage applied to the probe; a receiving circuit unit that amplifies a received signal from the probe; an ultrasonic image forming unit that forms an ultrasonic image on the basis of ultrasonic image data from the receiving circuit unit; and a display unit that displays the ultrasonic image. A source follower circuit of a field effect transistor (hereinafter, an FET) is used for the transmitter circuit unit, and the source follower circuit supplies an arbitrary voltage to the probe by controlling a gate voltage of the FET.

In addition, in the invention, the transmitter circuit unit includes: the plurality of source follower circuits connected to each other; a control section for controlling the gate voltage of each of the plurality of source follower circuits connected to each other; and a power supply section which applies a voltage, which is lower than a power supply voltage, to a drain of each FET through a diode.

In addition, in the invention, the transmitter circuit unit includes: the plurality of source follower circuits connected to each other; a control section which makes gate connections of the FETs of the plurality of source follower circuits connected to each other to control the voltage of the gate; and a power supply section which applies a voltage, which is lower than a power supply voltage, to a drain of each FET through a diode.

In addition, in the invention, a current source for making a bias current flow through a source of the source follower circuit is formed using the same type of FET as the source follower circuit.

In addition, a constant current source for biasing of the source follower circuit is provided in a plural number, and one of the constant current sources for biasing is connected to a predetermined voltage supply, and the other constant current sources for biasing are connected to voltage supplies, which have higher voltages and different levels than the predetermined voltage supply, with diodes therebetween.

In addition, in order to achieve the above-described object, in the invention, there is provided a carrier signal generating circuit that generates an ultrasonic signal applied to a probe of an ultrasonic diagnostic apparatus which transmits and receives an ultrasonic wave to and from an object and forms an ultrasonic image on the basis of received ultrasonic image data. A source follower circuit of an FET is used, and the source follower circuit supplies an arbitrary voltage to the probe by controlling a gate voltage of the FET.

Similarly, in order to achieve the above-described object, in the invention, there is provided a carrier signal generating circuit that generates an ultrasonic signal applied to a probe of an ultrasonic diagnostic apparatus which transmits and receives an ultrasonic wave to and from an object and forms an ultrasonic image on the basis of received ultrasonic image data. An emitter-follower circuit of a bipolar transistor is used, and an arbitrary voltage is supplied to the probe by controlling a base voltage of the bipolar transistor.

Advantageous Effects of Invention

As described above, according to the ultrasonic diagnostic apparatus using the carrier signal generating circuit of the invention, the following effects are obtained.

(1) Since a configuration using a source follower circuit of a transistor is adopted, an arbitrary output waveform can be generated by controlling the gate voltage of the transistor.

(2) Since a configuration using only one kind of transistor is adopted, the manufacturing process for IC implementation is simple and the cost can be reduced. In particular, in the case of using an NMOSFET, the effect is large in the operating speed and the manufacturing process.

(3) Since a transistor corresponding to each channel can be replaced with a transistor with a low withstand voltage by adopting a multi-stage configuration (so-called cascade connection), the size of the transistor can be reduced (space can be reduced) and the cost can be reduced.

(4) Since power supplies of transistors in a multi-stage configuration can be automatically changed according to the output voltage, power consumption can be reduced. This reduces heat or noise.

DESCRIPTION OF EMBODIMENTS

Hereinafter, embodiments of the invention will be described in detail according to the drawings. First, the basic configuration of an ultrasonic diagnostic apparatus to which the invention is applied will be described.

Figure 1:
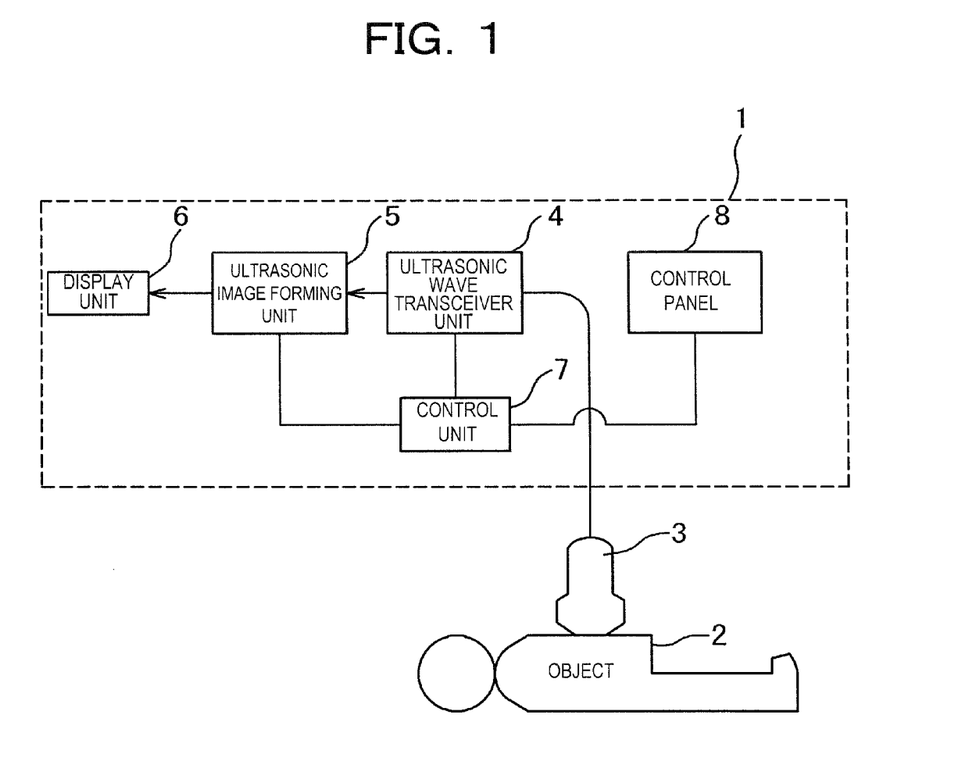
FIG. 1 is a block diagram showing an example of the entire configuration of an ultrasonic diagnostic apparatus to which the invention is applied.

FIG. 1 is a block diagram showing the basic configuration of an ultrasonic diagnostic apparatus. An ultrasonic diagnostic apparatus 1 forms and displays a two-dimensional ultrasonic image or a three-dimensional ultrasonic image for a portion to be diagnosed using a reflected echo signal obtained by transmitting to or receiving an ultrasonic wave from an object 2. The ultrasonic diagnostic apparatus 1 includes: an ultrasonic probe 3 including a plurality of transducer elements which irradiates the object 2 with an ultrasonic signal and receives the ultrasonic signal; an ultrasonic wave transceiver unit 4 that transmits or receives an ultrasonic signal; an ultrasonic image forming unit 5 that forms a two-dimensional ultrasonic image (B-mode image) or a three-dimensional ultrasonic image on the basis of the received signal; a display unit 6, which includes a display that displays the ultrasonic image formed by the ultrasonic image forming unit 5; a control unit 7 that controls each component; and a control panel 8 which gives an instruction to the control unit 7. In such an ultrasonic probe 3, a plurality of transmission signal amplifiers is required.

The invention provides a transmitter circuit, which transmits an ultrasonic wave, of the ultrasonic wave transceiver unit 4, in particular, a carrier signal generating circuit suitable for IC implementation. In addition, the transmitter circuit may be called a carrier signal generating circuit or a transmitter circuit section.

First Embodiment

First, the carrier signal generating circuit of a first embodiment will be described on the basis of FIG. 2.

Figure 2:
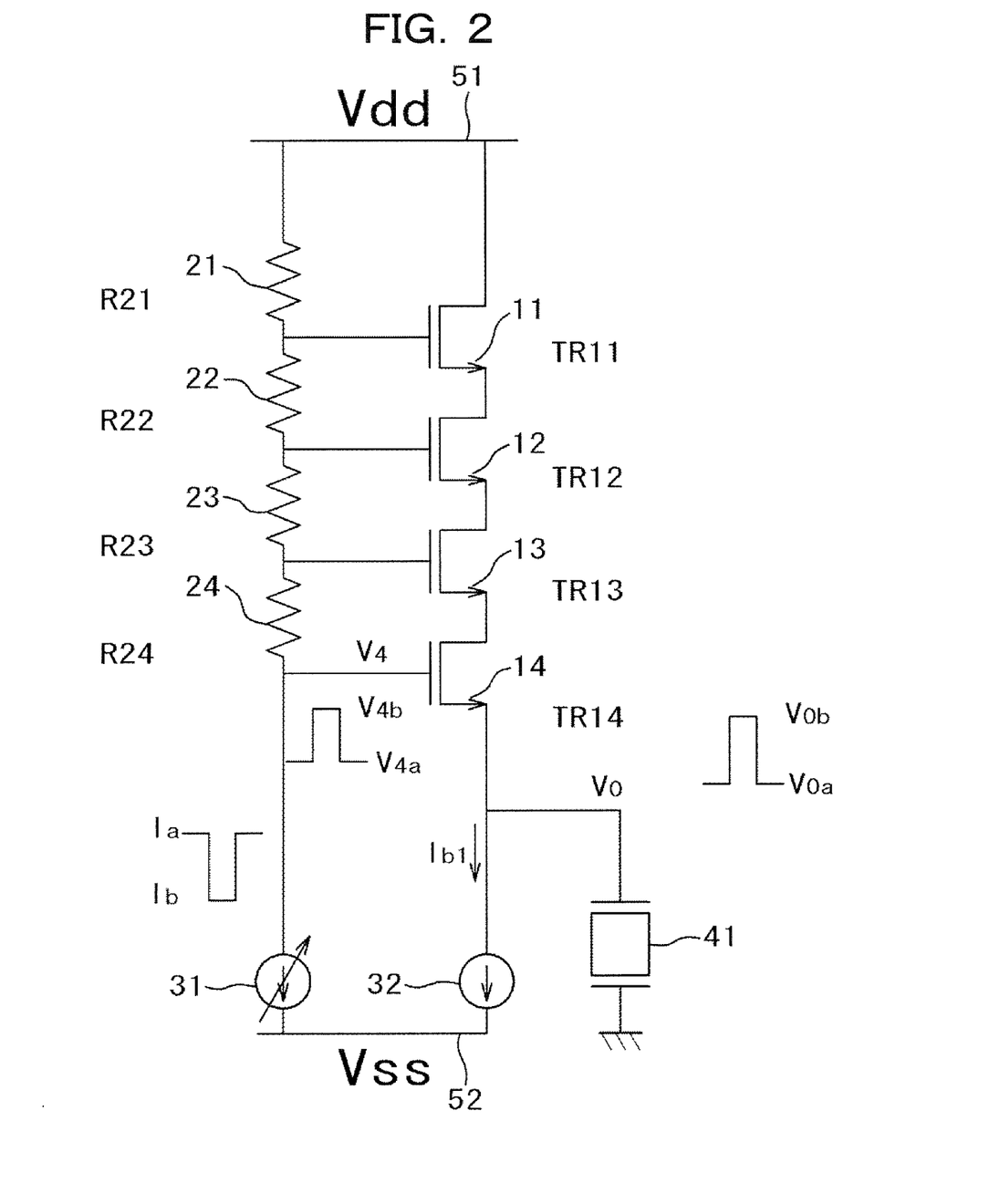
FIG. 2 is a view showing a transmitter circuit which generates a carrier signal to a probe according to a first embodiment.

FIG. 2 is a view showing a carrier signal generating circuit for one channel. In FIGS. 2, 11 to 14 are source follower type NMOSFETs (TR11 to TR14) connected to each other in a multi-stage manner (so-called a cascade connection), 21 to 24 are resistors with resistance of R21 to R24, 31 is a variable current source, 32 is a constant current source for biasing, and 41 is a probe for 1 channel. In addition, 51 and 52 are DC power supplies Vdd and Vss, respectively. For example, they are +100 V and −100 V, respectively.

When a pulse current Is with a current value changing from Ia to Ib is generated by the variable current source 31, a gate voltage V4 of the NMOSFET 14 changes from $V4a=Vdd-(R21+R22+R23+R24)Ia$ to $V4b=Vdd-(R21+R22+R23+R24)Ib$. As a result, a voltage of $Vo=V4-Vgs4$ appears as a source voltage Vo of the NMOSFET 14. Here, Vgs4 is a gate-to-source voltage of the NMOSFET 14. Generally, when Ib1 is constant, Vgs4 is almost constant and is small. Approximately, $Vo \cong V4$. By controlling the output current of the variable current source 31 in this way, it is possible to generate a voltage with arbitrary amplitude in the probe 41. In addition, since a voltage (voltage between a source and a drain) applied to each NMOSFET is divided by connecting the NMOSFETs to each other in multiple stages, withstand voltages of the NMOSFETs 11 to 14 may be small. For example, when R21 to R24 are equal and Vdd=100 V, Vss=−100 V, and Vo=−60 V, the voltage applied to each NMOSFET is about 40 V.

Thus, in the carrier signal generating circuit of the present embodiment, a waveform with arbitrary amplitude can be generated. In addition, since an NMOSFET which has a low withstand voltage due to cascade connection is used and the carrier signal generating circuit can be formed only by NMOSFETs, the carrier signal generating circuit has a small size. Accordingly, since the IC manufacturing process is easy, it is possible to provide a carrier signal generating circuit at low cost.

Second Embodiment

Next, a second embodiment will be described using FIG. 3A. The second embodiment is different from the first embodiment in that power supplied to the NMOSFETs 11 to 14 changes with a voltage of a transmission pulse output to the probe 41. Since supplied power changes automatically according to the voltage, power consumption can be reduced.

Hereinafter, the configuration and operation of the carrier signal generating circuit of the present embodiment will be described in detail.

Figure 3A:
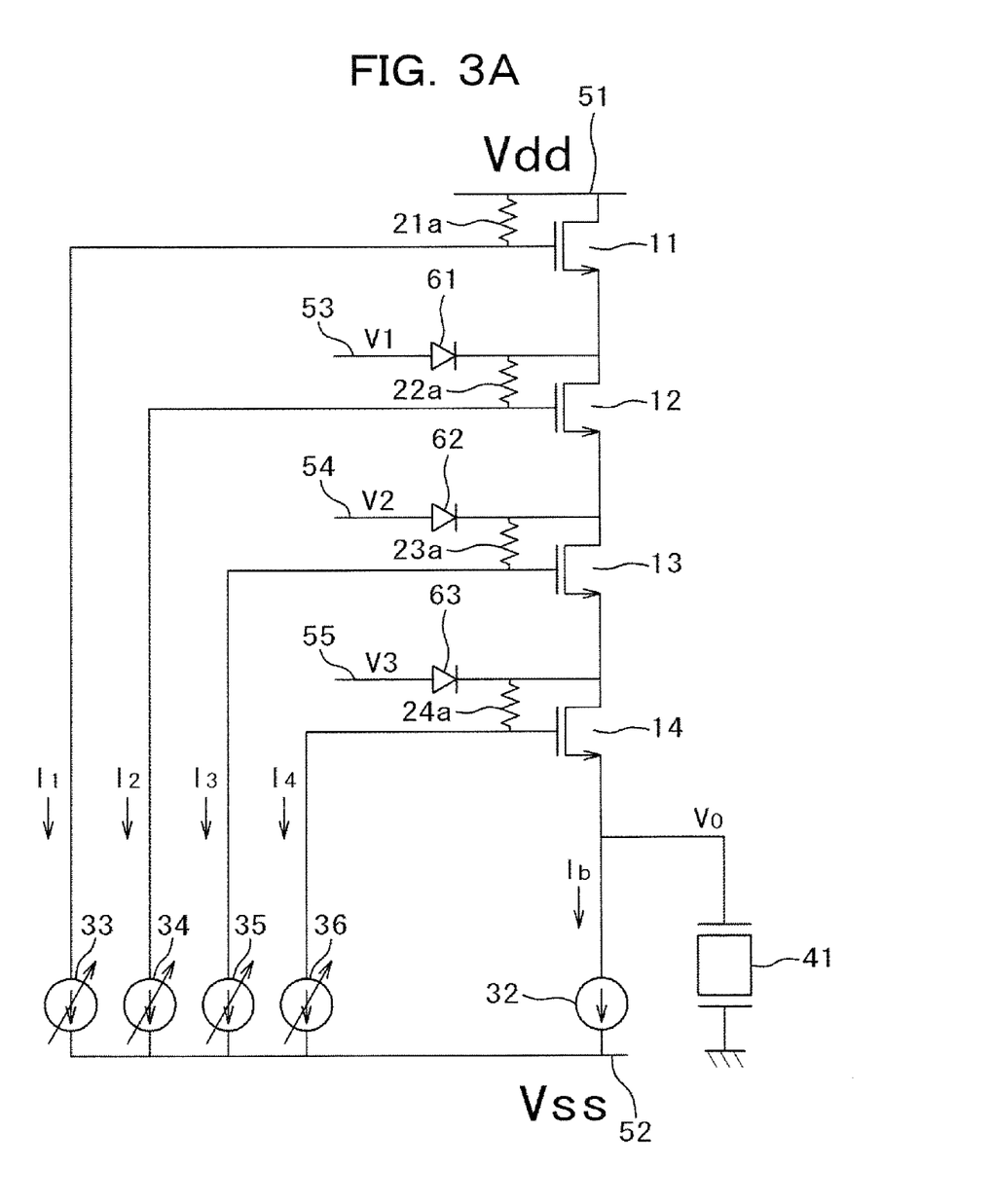
FIG. 3A is a view showing a transmitter circuit which generates a carrier signal to a probe according to a second embodiment.

In FIG. 3A, reference numerals 53 to 55 are power supplies V1 to V3 newly provided, and the power supplies V1 to V3 supply constant voltages with the relationship of Vdd>V1>V2>V3. By control of diodes 61 to 63 and variable current sources 33 to 36, a power supply to be used is automatically selected according to a desired output voltage. For example, in the case of an output with a lower level than V3, the current source 36 is controlled to obtain a predetermined output voltage Vo ($\cong Vdd-R24a*14$). In this case, in order to remove power consumption at the NMOSFETs 11 to 13, the NMOSFETs 11 to 13 are controlled such that the NMOSFETs 11 to 13 are turned off. For example, in order to turn off the NMOSFET 13, the NMOSFET 13 is controlled such that the gate voltage of the NMOSFET 13 becomes lower than V3 by several volts. The same is true for the NMOSFETs 11 and 12. Control of the current sources 33 to 36 is performed by the control unit 7.

For easier understanding, explanation using numeric values will be given. For example, it is assumed that Vdd=100 V, Vss=−100 V, resistors 21a to 24a=10 kΩ, V1=70 V, V2=40 V, and V3=10 V. In addition, it is assumed that the forward voltage of each of the diodes 61 to 63 is 0 V for the sake of convenience and the gate-to-source voltage when each of the NMOSFETs 11 to 14 is turned on is 0 V. In this state, the case of generating the waveform of the output voltage Vo shown in FIG. 3B is considered.

Figure 3B:
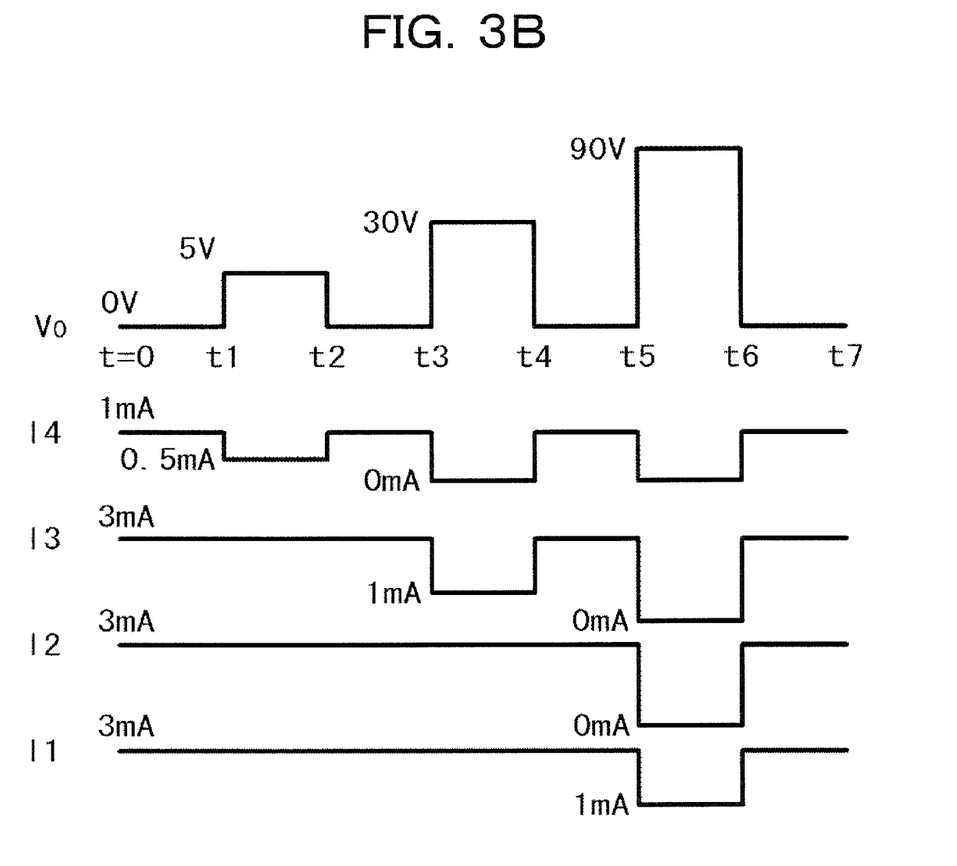
FIG. 3B is a view showing an example of an operation waveform of the transmitter circuit according to the second embodiment.

(1) During a period of t=0 to t1 in FIG. 3B, Vo=0 V. Accordingly, it is preferable to supply a current from V3 (=10 V). For this reason, I4 is set to 1 mA. On the other hand, by setting the gate voltage of the FET 13 to be equal to or smaller than 10 V by making a current of 3 mA or more flow as I1 to I3, the FET 13 can be made to have a cut-off state.

(2) During a period of t=t1 to t2, Vo=5 V. Accordingly, it is preferable to supply a current from V3 in the same manner as in (1) described above. In order to obtain Vo=5 V, I4=0.5 mA is made to flow. On the other hand, similarly to the above, a current of 3 mA or more for holding the FET 13 in the cut-off state is made to flow as I1 to I3.

(3) During a period of t=t3 to t4, Vo=30 V. Accordingly, the current is supplied from V2 (=40 V). For this reason, I4=0 is set to make the FET 14 have a diode connection state, and I3=1 mA is set. On the other hand, in order to make the FET 12 have a cut-off state, a current of 3 mA or more is made to flow as I1 and I2.

(4) Finally, since V=90 V from t5 to t6, the current is supplied from Vdd (=100 V). For this reason, I1 is set to 1 mA. On the other hand, I2 to I4 are set to 0 mA in order to make the FETs 11 to 14 have a diode connection state.

Thus, electric power supplied to a load can be controlled by controlling the currents of the variable current sources 33 to 36 according to the output voltage. As a result, power consumption can be suppressed. Such power savings are effective when the number of probes is very large (may be several thousands of channels) as in the two-dimensional probe. The voltage, waveform, frequency, and the like of a transmission signal depend on a part to be imaged, depth, and a probe to be used. Therefore, the effect can be realized by controlling the current of the variable current source by a signal from a control unit or the like.

Third embodiment

In addition, a third embodiment will be described on the basis of FIG. 4.

In the same manner as in the second embodiment, supplied power can be automatically changed by a variable current source 37. Control of the variable current source 37 is performed by a control signal from a control unit.

Hereinafter, an operation of a carrier signal generating circuit of the present embodiment will be described in detail.

Figure 4:
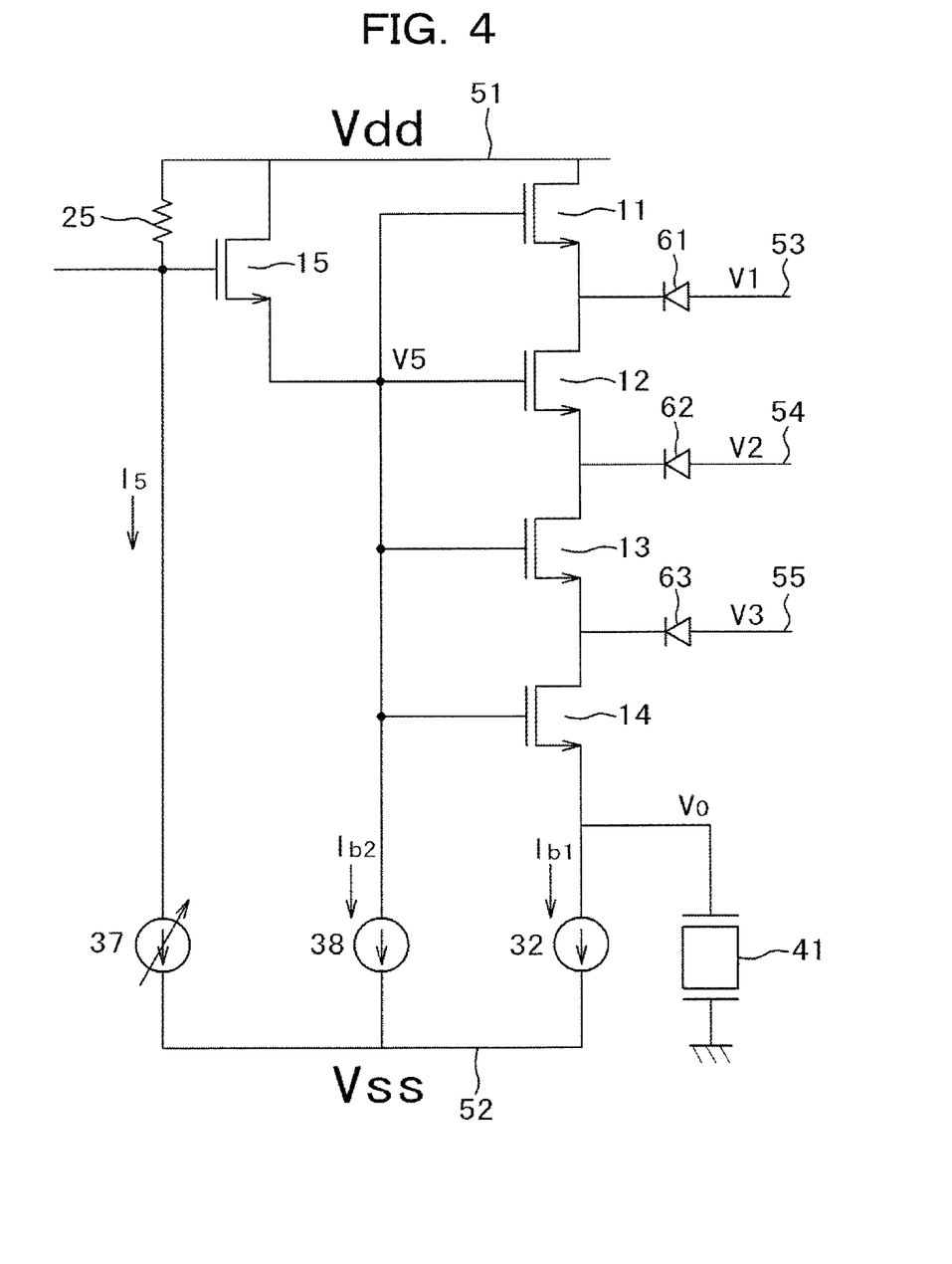
FIG. 4 is a view showing a transmitter circuit which generates a carrier signal to a probe according to a third embodiment.

In FIG. 4, gates of NMOSFETs 11 to 14 are short-circuited and are driven by an NMOSFET 15 functioning as a control circuit. Accordingly, since the NMOSFET 15 and the NMOSFETs 11 to 14 form a so-called Darlington connection, driving by the variable current source 37 and the resistor 25 can be realized with low electric power. In addition, the variable current source 37 is controlled by a control signal from the control unit 7 in FIG. 1, for example. In addition, also in this circuit, appropriate voltage supply is automatically selected according to the output voltage of the NMOSFET 15.

For example, when a voltage V5 at the time when I5 is made to flow through the resistor 25 is V2<V5<V1, the gate voltage V5 of the NMOSFET 11 is lower than V1, the NMOSFET 11 is turned off. On the other hand, since the gate voltage V5 of the NMOSFET 12 is higher than V2, the NMOSFET 12 is turned on and the diode 62 is turned off. Similarly, the NMOSFETs 13 and 14 are turned on and the diode 63 is turned off. Thus, only the voltage V1 is selected.

According to the configuration of the present embodiment, this is the same for other levels. Accordingly, since an appropriate power supply is selected according to the output of the variable current source 37, power consumption is low. In addition, since only one variable current source is used, control is easy.

Fourth Embodiment

Figure 5A:
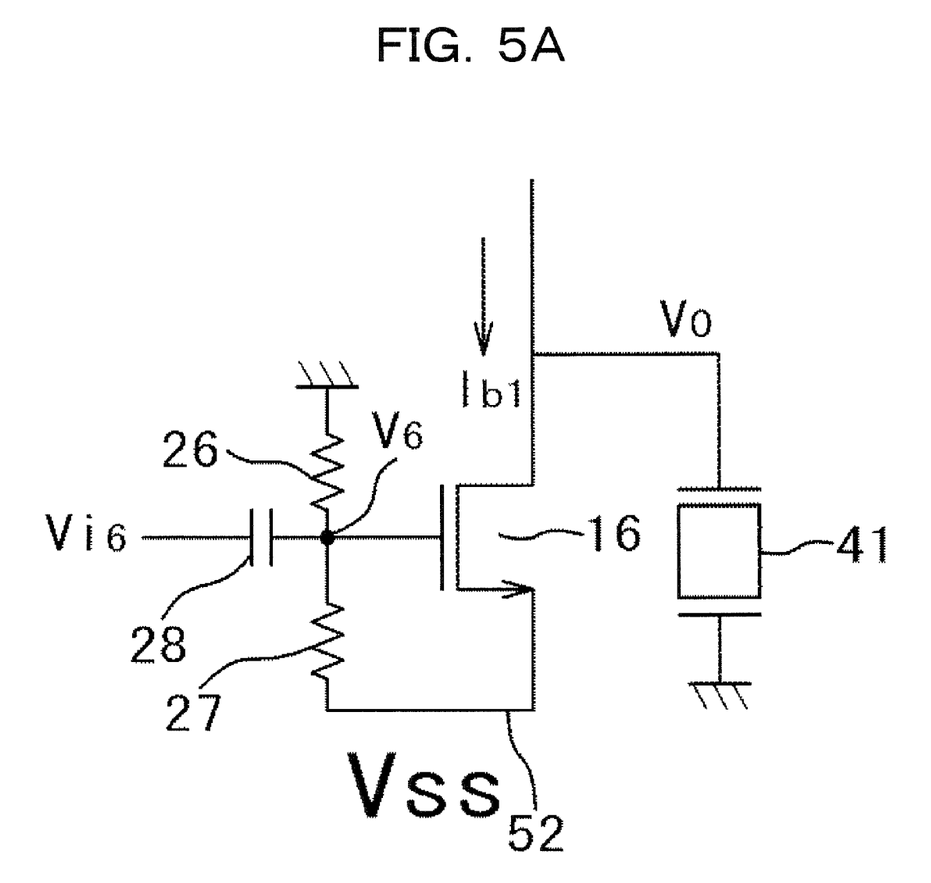
FIG. 5A is a view showing a constant current source circuit for biasing of a transmitter circuit according to a fourth embodiment.
Figure 5B:
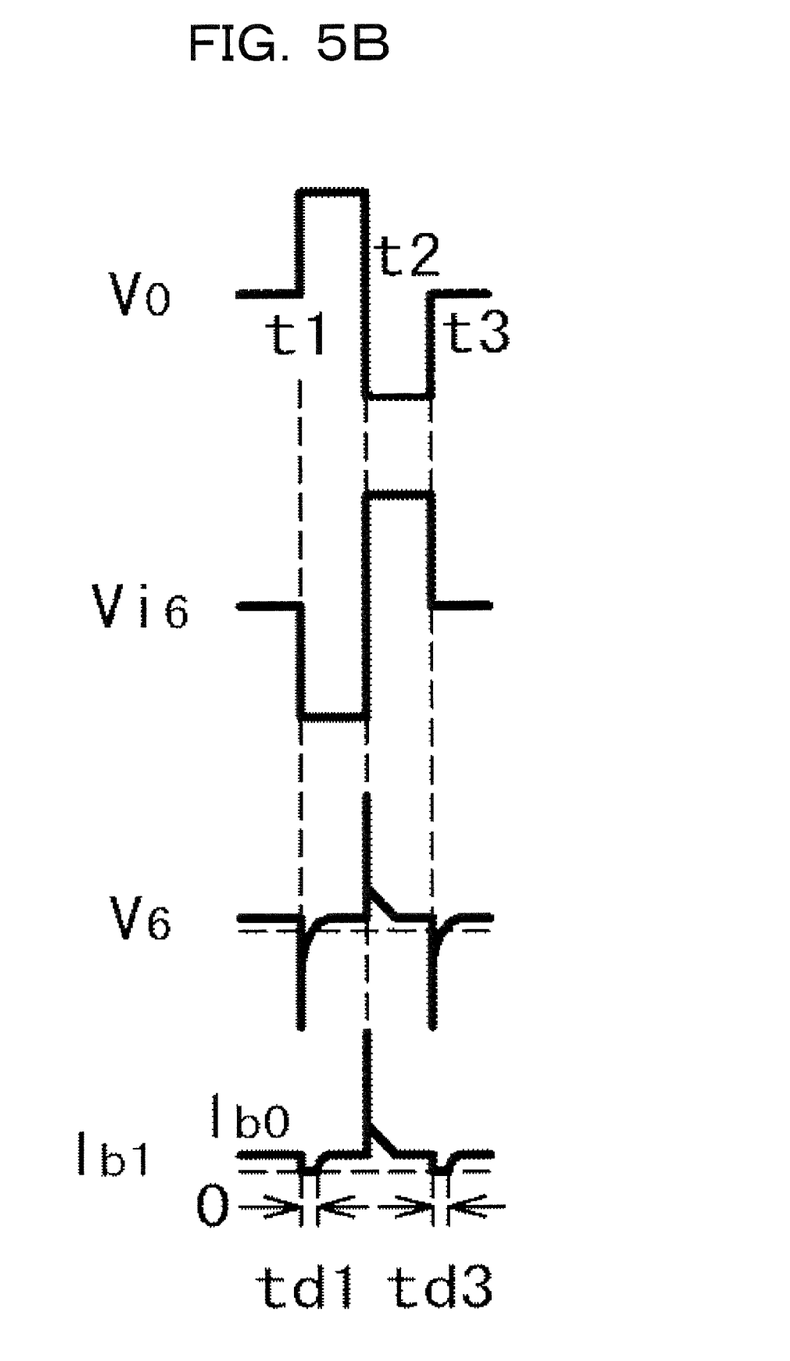
FIG. 5B is a view showing an example of an operation waveform of the constant current source circuit for biasing of the transmitter circuit according to the fourth embodiment.

In the first to third embodiments described above, the constant current source for biasing 32 is used to make the bias current Ib1 of a source follower flow. However, this constant current source circuit for biasing can be realized as shown in FIG. 5A, for example. An example of timing of the waveform in the embodiment of the constant current source for biasing is shown in FIG. 5B.

FIG. 5A shows an N type FET (NMOSFET 16) which is of the same type as an FET, in which a source follower circuit is used for the constant current source for biasing, as an example. In order to make the small DC bias current Ib1 flow through the NMOSFET 16, an appropriate bias voltage is applied to the gate of the NMOSFET 16 using a voltage divider formed by resistors 26 and 27. Since a probe is usually a capacitive load, large charge and discharge currents flow instantaneously only at the rising and falling edges of the voltage Vo. The charge current is supplied from the source follower of the NMOSFET 14, and the discharge current is pulled by the constant current source for biasing. Accordingly, by supplying a voltage Vi6 with a waveform of an opposite phase to the waveform of the voltage Vo to the bias point of the resistors 26 and 27 through a capacitor 28 such that a large current flows only at the falling edge of the voltage Vo, the voltage Vi6 rises when the voltage Vo falls (t=t2). As a result, since the NMOSFET 16 is turned on, it is possible to make a large current flow through the NMOSFET 16. On the other hand, at the rising edge of the voltage Vo (t=t1 and t3), the gate voltage of the NMOSFET 16 falls. As a result, a current does not flow during a period for which the voltage is equal to or lower than the threshold voltage of the NMOSFET, that is, a period of td1 and td3.

Thus, according to the constant current source circuit for biasing of the present embodiment, a large current can be made to flow only at the falling edge while making a small current flow during a period for which a pulse is being transmitted. As a result, power consumption can be reduced.

Fifth Embodiment

Figure 6A:
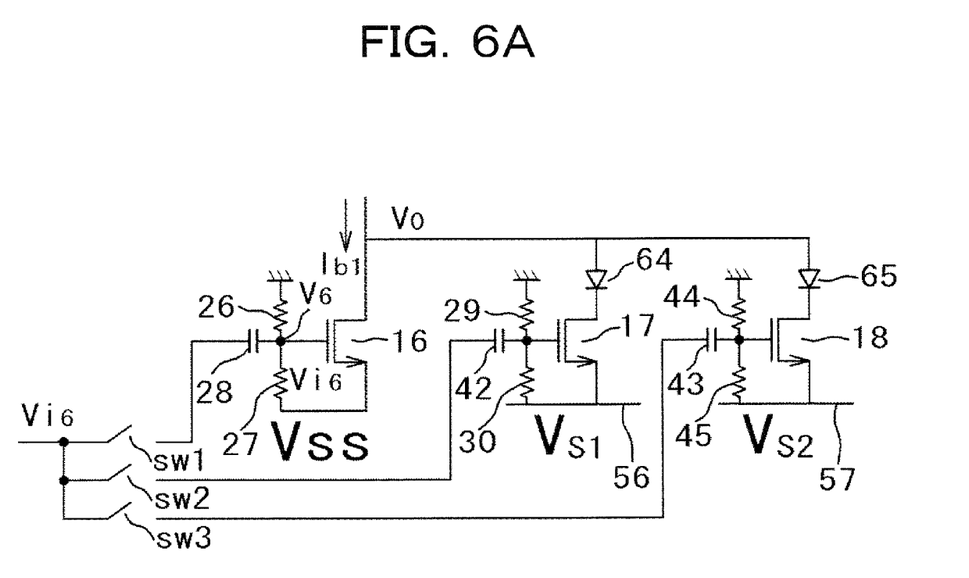
FIG. 6A is a view showing a constant current source circuit for biasing of a transmitter circuit according to a fifth embodiment.

In the fourth embodiment described above, only one constant current source for biasing using the NMOSFET 16 is used and connected to the predetermined power supply Vss. However, as shown in FIG. 6A, it is also possible to prepare a plurality of constant current sources for biasing using NMOSFETs 16, 17, and 18 and to connect them to different voltage supplies Vss, Vs1, and Vs2 (Vss<Vs1<Vs2) so that an appropriate constant current source for biasing can be selected according to the output voltage. In this case, power consumption can be further reduced.

Here, diodes 64 and 65 are provided to keep a current from flowing in the reverse direction in the NMOSFETs 17 and 18 when the output voltage Vo is lower than Vs1 and Vs2. The configuration of the fifth embodiment 5 will be described in detail using a block diagram of FIG. 6A and a timing chart of FIG. 6B. Here, it is assumed that Vss=−100 V, Vs1=−60 V, and Vs2=−20 V.

(1) For example, when Vo is equal to or higher than −20 V, only the NMOSFET 18 operates, that is, a current flows through the voltage supply Vs2. Thus, power consumption is suppressed.

Figure 6B:
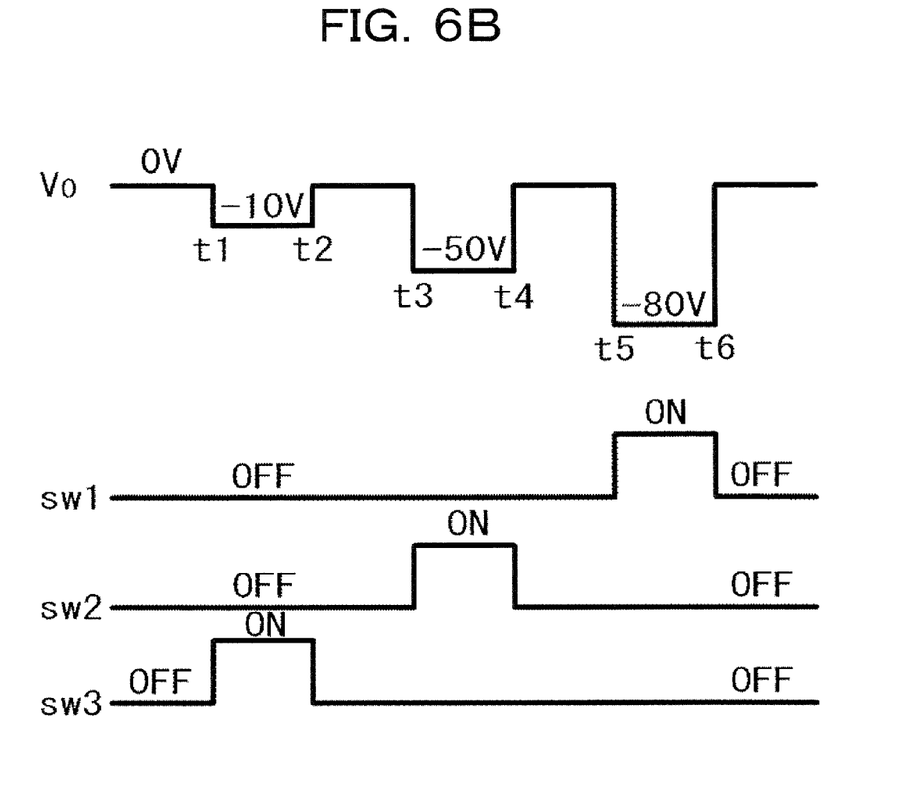
FIG. 6B is a view showing an example of an operation waveform of the constant current source circuit for biasing of the transmitter circuit according to the fifth embodiment.

(2) As shown in FIG. 6B, during a period of t=t3 to t4, Vo=−50 V. Accordingly, Vs1 (=−60 V) is used. For this reason, sw2 is turned on for only the period of t=t3 to t4.

(3) During a period of t=t5 to t6, Vo=−80 V. Accordingly, Vss (=−100 V) is used. For this reason, sw1 is turned on for only the period of t=t5 to t6.

In addition, although the source follower type NMOSFETs were used as transistors for transmission wave amplifiers in the explanation of the above embodiment, the circuit configuration may be changed by using an emitter-follower type bipolar transistor instead. In this case, it is preferable to control the base voltage instead of the gate voltage.

INDUSTRIAL APPLICABILITY

The invention is useful as an ultrasonic diagnostic apparatus which forms a tomographic image or the like of a body with a received signal obtained by transmitting an ultrasonic wave to the body and in particular, as a signal transmission technique of generating an arbitrary waveform of a transmission signal applied to an ultrasonic probe.

REFERENCE SIGNS LIST

1: ultrasonic diagnostic apparatus
2: object
3: ultrasonic probe
4: ultrasonic wave transceiver unit
5: ultrasonic image forming unit
6: display unit
7: control unit
8: control panel
11 to 18: N type MOSFET
21 to 30, 44, 45: resistor
28, 42, 43: capacitor
31 to 38: current source
41: probe
51 to 57: DC current source
61 to 65: diode

The invention claimed is:

1. An ultrasonic diagnostic apparatus comprising:
a probe which transmits and receives an ultrasonic wave to and from an object;
a transmitter circuit unit connected to a controller and the probe,
wherein the transmitter circuit unit supplies a voltage to the probe by using a signal transmitted from the controller;
a receiving circuit unit connected to the probe,
wherein the receiving circuit amplifies a received signal from the probe, and
wherein an ultrasonic image is formed based on ultrasonic image data from the receiving circuit unit; and
a display that displays the ultrasonic image,
wherein the transmitter circuit unit comprises:
a first variable current source connected to the controller such that the output current is controlled by the controller;
a first resistor connected in series to the first variable current source;
a first FET connected in parallel to the first variable current source and the first resistor,
wherein a gate of the first FET is connected to a first connecting point of the first resistor and the first variable current source;
a first direct current source,
wherein a positive or negative first side of the first direct current source is connected to a second connecting point of the first resistor and a source of the first FET, and a second side of the first direct current source is connected to a third connecting point of the first variable current source and drain of the first FET, and
wherein the probe is connected to a drain of the first FET;
a second FET disposed between the first side of the first direct current source and a source of the first FET,
wherein a drain of the second FET is connected to a positive or negative third side of a second direct current source via a first diode;
a second resistor disposed between a gate and a source of the second FET; and
a second variable current source disposed between the gate of the second FET and the second side of the first direct current source.

2. The ultrasonic diagnostic apparatus according to claim 1, wherein the transmitter circuit unit further comprises:
a third FET and a fourth FET connected in series,
wherein the fourth FET is disposed to the first side, and the third FET is disposed to the second side,
wherein a gate of the third FET and a gate of the fourth FET are connected to a drain of the first FET,
wherein a drain of a fourth FET is connected to a positive or negative fourth side of a third direct current source via a second diode, and
wherein the probe is connected to a drain of the third FET.

3. The ultrasonic diagnostic apparatus according to claim 2, wherein the transmitter circuit unit further comprises:
a third resistor disposed between the first side of the first direct current source and the first resistor; and
a fifth FET disposed between the first side of the first direct current source and the source of the first FET, and
wherein a first resistor side of the third resistor is connected to the gate of the third FET.

4. The ultrasonic diagnostic apparatus according to claim 1,
wherein the second direct current source is one of a plurality of second direct current sources, and
wherein one of the first direct current source or the second direct current source is connected to a predetermined voltage supply, and the other of the first direct current source or the second direct current source is connected to voltage supplies, which have higher voltages and different levels than the predetermined voltage supply, with diodes therebetween.

5. A transmitter circuit unit comprising:
a first variable current source connected to a controller such that the an output current is controlled by the controller;
a first resistor connected in series to the first variable current source;
a first FET connected in parallel to the first variable current source and the first resistor, wherein a gate of the first FET is connected to a first connecting point of the first resistor and the first variable current source;
a first direct current source,
wherein a positive or a negative first side is connected to a second connecting point of the first resistor and a source of the first FET, and a second side is connected to a third connecting point of the first variable current source and drain of the first FET, and
wherein the probe is connected to the drain of the first FET.

6. An ultrasonic diagnostic apparatus comprising:
a probe which transmits and receives an ultrasonic wave to and from an object;
a transmitter circuit unit, connected to a controller and the probe,
wherein the transmitter circuit unit supplies a voltage to the probe by using a signal transmitted from the controller;
a receiving circuit unit connected to the probe,
wherein the receiving circuit amplifies a received signal from the probe, and
wherein an ultrasonic image is formed based on ultrasonic image data from the receiving circuit unit; and
a display that displays the ultrasonic image,
wherein the transmitter circuit unit comprises:
a first variable current source connected to the controller such that the output current is controlled by the controller;
a first resistor connected in series to the first variable current source;
a first bipolar transistor connected in parallel to the first variable current source and the first resistor,
wherein a base of the first bipolar transistor is connected to a first connecting point of the first resistor and the first variable current source; and
a first direct current source,
wherein a positive or negative first side is connected to a second connecting point of the first resistor and a collector of the first bipolar transistor, and the second side is connected to a third connecting point of the first variable current source and an emitter, of the first bipolar transistor, and
wherein the probe is connected to the emitter of the first bipolar transistor.

* * * * *